(12) United States Patent
Park et al.

(10) Patent No.: US 7,485,450 B2
(45) Date of Patent: Feb. 3, 2009

(54) TDCBC/PCKA GENE-INACTIVATED MICROORGANISM AND METHOD OF PRODUCING L-THREONINE USING THE SAME

(75) Inventors: Young Hoon Park, Gyeonggi-do (KR); Byoung Choon Lee, Seoul (KR); Dae Cheol Kim, Gyeonggi-do (KR); Jin Ho Lee, Gyeonggi-do (KR); Jae Yong Cho, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 303 days.

(21) Appl. No.: 10/817,044

(22) Filed: Apr. 2, 2004

(65) Prior Publication Data

US 2004/0241831 A1 Dec. 2, 2004

(51) Int. Cl.
*C12N 1/20* (2006.01)
(52) U.S. Cl. .................................. 435/252.3
(58) Field of Classification Search ............ 435/252.33, 435/4, 320.1, 462, 252.3
See application file for complete search history.

(56) References Cited

U.S. PATENT DOCUMENTS 4,278,765 A * 7/1981 Debabov et al. ............ 435/481
5,919,694 A * 7/1999 Sugimoto et al. ...... 435/252.33
6,107,063 A * 8/2000 Moeckel et al. ............. 435/116
6,420,151 B1 * 7/2002 Eikmanns et al. ........... 435/194

FOREIGN PATENT DOCUMENTS

EP 1347057 A1 * 9/2003

OTHER PUBLICATIONS

Ozaki et al. Agric. Biol. Chem. 47 No. 7 (1983) 1569-1576.*
Benjamin Lewin Genes IV., 1990, p. 810 Definition of a "gene".*
Palmeros et al 2000 Gene 247 255-264.*

* cited by examiner

*Primary Examiner*—Mark Navarro
*Assistant Examiner*—Nina A Archie
(74) *Attorney, Agent, or Firm*—Arent Fox LLP

(57) ABSTRACT

The present invention provide a microorganism comprising an inactivated chromosomal tdcBC gene and an inactivated chromosomal pckA gene, which has remarkably improved productivity of L-threonine. Also, the present invention provides a method of producing L-threonine using the microorganism. The microorganism is prepared by incorporating by a recombination technique an antibiotic resistance gene into a pckA gene on the chromosome of a bacterial strain containing an L-threonine degradation-associated operon gene, tdcBC, which is inactivated. The microorganism has the effect of preventing degradation and intracellular influx of L-threonine due to the inactivation of the tdcBC operon gene, and includes more activated pathways for L-threonine biosynthesis. Therefore, the microorganism is useful for mass production of L-threonine because of being capable of producing L-threonine in high levels and high yields even in the presence of high concentrations of glucose.

1 Claim, 3 Drawing Sheets

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Forward primer for PCR

<400> SEQUENCE: 1
gttaacaccc ccaaaaagac                                              20

<210> SEQ ID NO 2
<211> LENGTH: 21
<212> TYPE: DNA
<213> ORGANISM: Artificial Sequence
<220> FEATURE:
<223> OTHER INFORMATION: Reverse primer for PCR

<400> SEQUENCE: 2
gataaagagt tcgcagttcg t                                            21

TDCBC/PCKA GENE-INACTIVATED MICROORGANISM AND METHOD OF PRODUCING L-THREONINE USING THE SAME

This application claims priority to Korean Patent Application No. 10-2003-0021458 filed Apr. 4, 2003, the contents of which are incorporated herein in their entirety by reference The present invention relates to an L-threonine-producing microorganism and a method of producing an L-threonine-producing microorganism. More particularly, the present invention relates to a microorganism that contains an inactivated, chromosomal tdcBC gene and an inactivated, chromosomal pckA gene. Microorganisms of the invention display remarkably improved productivity of L-threonine due to the inactivation of the two genes. Also provided is a method of producing L-threonine using such a microorganism.

BACKGROUND OF THE INVENTION

L-threonine is known to be an essential amino acid, which has been widely used as an additive to animals' fodder and foods and an animal growth stimulator, as well as a component of medical aqueous solutions and other raw material for medicinal products. L-threonine is currently produced by only five companies in advanced countries, including the Ajinomoto Company in Japan, and is two to three times more expensive than lysine that is known to be highly valuable due to it high price of 5,000-6,000 dollars per ton in the international market. Thus, L-threonine has high growth potential in the world market.

L-threonine is currently produced by microbial fermentation techniques, using mainly mutants derived from wild types of microorganisms, including *Escherichia coli*, the genus *Corynebacterium*, the genus *Brevibacterium*, the genus *Serratia* and the genus *Providencia*. Examples of these mutants include those having resistance to amino acid analogues or drugs, and their auxotrophs for diamino-pimelic acid, methionine, lysine and isoleucine (Japanese Pat. Publication No. Heisei 2-219582; Korean Pat. Application No. 1998-32951; *Appl. Microbiol. Biotechnol.*, 29:550-553, 1988). However, such mutant strains are disadvantageous in terms of having low L-threonine productivity and being limited to growth on media supplemented with expensive diamino-pimelic acid or isoleucine due to their auxotrophic properties for the diamino-pimelic acid or isoleucine. That is, in the case of using a mutant requiring diamino-pimelic acid for growth, this fermentative production of L-threonine is costly. Likewise, in the case of using an isoleucine auxotroph, a fermentation medium for this auxotroph must be supplemented with expensive isoleucine, resulting in increased production costs of L-threonine.

These problems may be overcome with an isoleucine-leaky mutant. For example, Korean Pat. Publication No. 92-8365 discloses an isoleucine-leaky mutant that does not need isoleucine in its medium and produces higher levels of L-threonine than known strains. However, this classical mutation method is also time-consuming and ineffective in selecting novel bacterial strains capable of producing high levels of L-threonine. In addition, its greatest disadvantage is being limited in improvement of L-threonine productivity.

In this regard, instead of employing auxotrophs, other methods for mass production of L-threonine have been developed. These methods employ metabolic engineering techniques to obtain recombinant L-threonine-producing microorganisms that have increased activity of enzymes participating in the biosynthesis of L-threonine. That is, genes corresponding to enzymes involving in L-threonine metabolism are isolated using genetic recombination techniques, cloned into proper gene vehicles, and introduced into microbial mutants to improve L-threonine productivity of the mutants.

The present inventors previously developed a method of developing a L-threonine producing strain using such metabolic engineering techniques, as disclosed in Korean Pat. Application No. 2001-6976. Briefly, high yields of L-threonine can be achieved by employing a recombinant microorganism comprising (a) one or more chromosomal copies of a ppc gene encoding phosphoenol pyruvate carboxylase (hereinafter, referred to simply as "ppc"), which catalyzes the formation of oxaloacetate (OAA) from phosphoenol pyruvate (PEP) and (b) an operon including genes encoding aspartokinase 1-homoserine dehydrogenase (thrA), homoserine kinase (thrB) and threonine synthase (thrC), which catalyze the biosynthesis of L-threonine from aspartate.

L-threonine is synthesized from aspartate by a multi-step pathway, wherein the aspartate is formed from OAA converted by PPC from PEP. L-threonine biosynthesis is inhibited when glucose is present in relatively high levels in media in comparison with the bacterial growth rate and the overall rate of the tricarboxylic acid (TCA) cycle . In this situation, ppc gene expression is suppressed, while expression of a gene encoding PEP carboxykinase (hereinafter, referred to simply as "pckA"), which catalyzes the conversion of OAA into PEP is increased. The elevated levels of pckA result in the formation of PEP from OAA as the precursor for amino acid biosynthesis, wherein other by-products are synthesized from the PEP (Goldie H. Medina V., Mol. Gen. Genet., 220(2):191-196, 1990; Dan G. Fraenkel., *E.coli and Salmonella*, 12:142-150, 1996). Therefore, the pckA gene should be essentially inactivated in order to produce L-threonine in high levels by increasing the flux of metabolic pathways responsible for L-threonine synthesis.

On the other hand, several pathways for L-threonine degradation are known, which include the following three pathways. One involves a pathway initiated by threonine dehydrogenase yielding α-amino-β-ketobutyrate. The α-amino-β-ketobutyrate is either converted to acetyl-CoA and glycine or spontaneously degrades to aminoacetone that is converted to pyruvate. The second pathway involves threonine dehydratase yielding α-ketobutyrate which is further catabolized to propionyl-CoA and finally the TCA cycle intermediate, succinyl-CoA. The third pathway utilizes threonine aldolase (Neidhardt F. C. et al. *Escherichia coli and Salmonella: cellular and molecular biology*, 2nd ed. ASM press. Washington D.C., pp369-370). Among them, the threonine dehydratase is an operon that is expressed under hypoxia and high levels of threonine. The present inventors developed a microorganism with improved productivity of L-threonine by specifically inactivating this operon gene (tdcBC) via a genetic recombination technique (Korean Pat. Application No. 2002-015380).

On the other hand, International Pat. Publication No. WO 02/29080 A2 discloses a method of producing L-threonine using a pckA, gene-defective microorganism, which is prepared by introducing it into a wild type strain of the microorganism a recombinant vector carrying a partially deleted pckA gene. However, this microorganism is problematic with respect to production yield of L-threonine because pathways for degradation and intracellular influx of synthesized L-threonine are still activated in the microorganism.

SUMMARY OF THE INVENTION

Intensive and thorough research conducted by the present inventors has yielded methods of preparing a microorganisms that are capable of producing high levels of L-threonine, even when grown in a medium containing high concentrations of glucose, without degrading the L-threonine produced. The inventors have found that the problems encountered in the prior art may be overcome with microorganisms in which the endogenous chromosomal pckA gene is inactivated and the tdcBC operon is knocked out. These microorganisms have improved L-threonine productivity in comparison with the conventional L-threonine-producing microorganisms.

Therefore, the present invention provides a pckA gene-inactivated microorganism, which is prepared by introducing an antibiotic resistance gene into the chromosomal DNA of a parent E. coli strain producing high levels of L-threonine, such as an E. coli strain containing an inactivated tdcBC operon, by a DNA recombination technique. Since its chromosomal tdcBC operon is inactivated, the microorganism according to the present invention has the effect of preventing degradation and intracellular influx of L-threonine. In addition, due to the inactivation of the pckA gene involved in the inhibition of L-threonine synthesis, the microorganism of the present invention has more activated pathways for L-threonine biosynthesis. Therefore, the microorganism of the present invention may be useful for mass production of L-threonine because of being capable of producing L-threonine in high levels and high yields even in the presence of high concentrations of glucose.

BRIEF DESCRIPTION OF THE DRAWINGS

The objects, features and other advantages of the present invention will be more clearly understood from the following detailed description taken in conjunction with the accompanying drawings, in which.

DETAILED DESCRIPTION OF THE INVENTION

Figure 1:
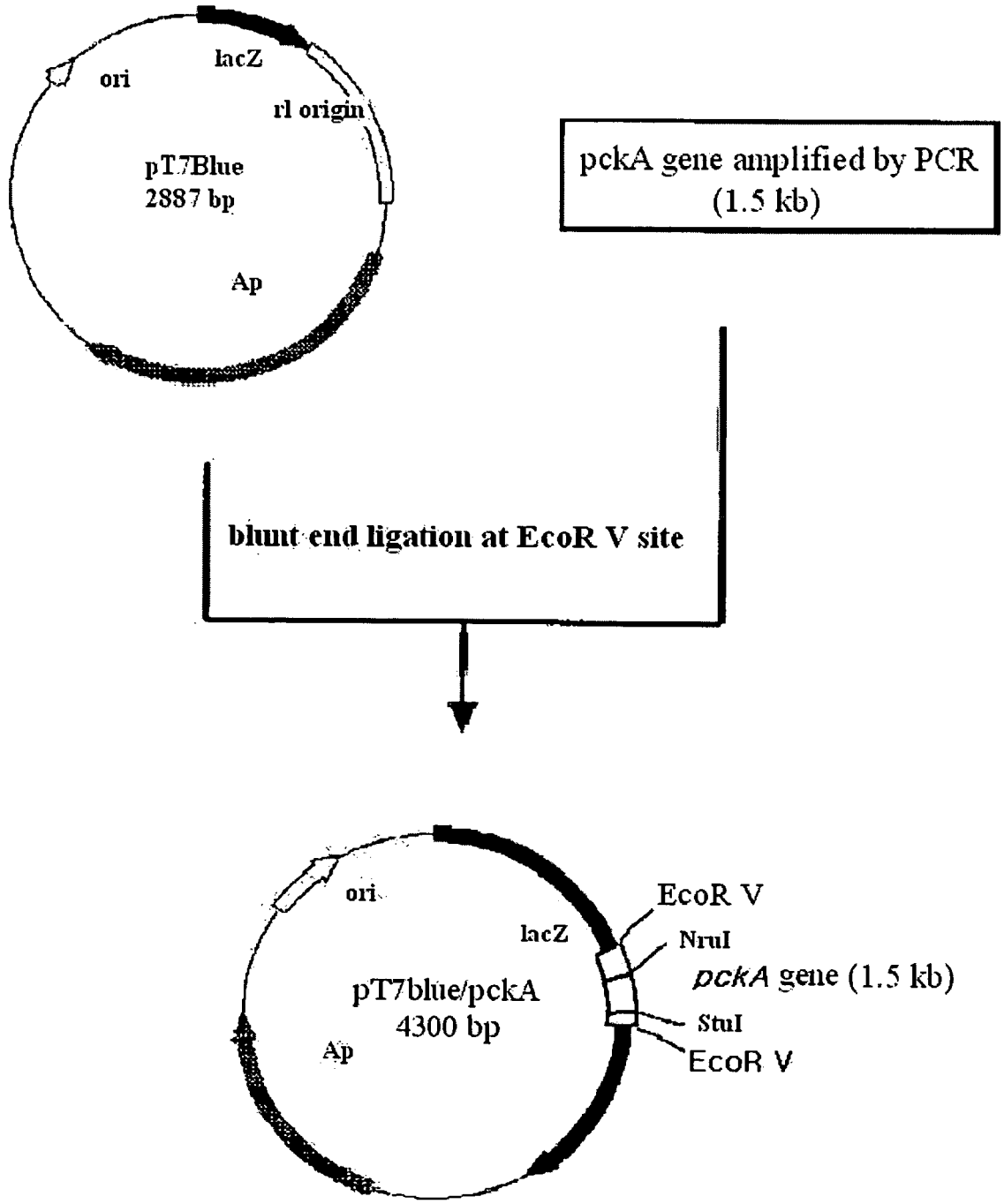
FIG. 1 is a schematic view showing a process of cloning apckA gene.

In order to accomplish the above objects, the present invention provides a novel strain of E. coli, in which the wild-type, endogenous, chromosomal tdcBC and pckA genes have been inactivated.

In the tdcBC/pckA gene-inactivated E. coli strain, the pckA gene is inactivated by introducing an exogenous pckA gene fragment that comprises an antibiotic resistance gene and a site-specific recombinase binding site at each of its ends into an E. coli strain containing an L-threonine degradation-associated operon, tdcBC that is inactivated, and then allowing homologous recombination to occur between the foreign exogenous pckA gene fragment and the wild-type, endogenous, chromosomal pckA gene, thereby inactivating the chromosomal pckA gene.

In addition, the present invention provides a method of producing L-threonine using the tdcBC/pckA gene-inactivated E. coli strain, so produced.

A strain of E. coli, which contains an L-threonine degradation-associated operon specifically inactivated by genetic recombination and has improved productivity of L-threonine due to the inactivation of the operon, may be used as a parent strain in the present invention. A preferred parent strain is E. coli strain TRN212 (accession number: KCCM-10353; Korean Pat. Application No. 2002-015380), which was developed by the present inventors.

The present invention is characterized by preparing a novel E. coli strain producing high levels and high yields of L-threonine by inactivating the pckA gene involved in inhibition of L-threonine synthesis in a parent E. coli strain containing an L-threonine degradation-associated operon (tdcBC) inactivated. The inactivation of both tdcBC and pckA genes results in the prevention of degradation and intracellular influx of L-threonine, mediated by the gene products of the tdcBC operon, and the inhibition of L-threonine synthesis, mediated by a gene product of the pckA gene, leading to high level production of L-threonine.

Therefore, the present invention provides a tdcBC/pckA gene-inactivated E. coli strain, which is prepared by introducing an exogenouspck pckA gene fragment that comprises an antibiotic resistance gene having a site-specific recombinase binding site at each of both ends into an E. coli strain containing an L-threonine degradation-associated operon, tdcBC, that is inactivated, and then allowing for homologous recombination between the foreign exogenous pckA gene fragment and a pckA gene on chromosome to inactivate the chromosomal pckA gene.

In addition, the pckA gene on chromosome of the parent E. coli strain is inactivated by removal of the antibiotic resistance gene incorporated into the chromosomal pckA gene by the activity of the site-specific recombinase expressed in the bacterial strain, and the presence of one copy of a binding site of the site-specific recombinase in the chromosomal pckA gene.

Inactivation of the pckA gene on the bacterial chromosome is achieved by homologous recombination with an exogenous pckA gene fragment. The foreign pckA gene fragment is inactivated by insertion of an antibiotic resistance gene thereinto. This foreign inactivated pckA gene fragment is introduced into a parent E. coli strain, and double crossover recombination is then allowed to occur between a pckA gene on the bacterial chromosome and the foreign inactivated pckA gene fragment to inactivate the pckA gene on the bacterial chromosome. The presence of the antibiotic resistance gene in the foreign inactivated pckA gene facilitates selection of pckA gene-inactivated cells.

According to the present invention, an "exogenous pckA gene fragment" may be any portion of the pckA gene that is (a) transcriptionally and/or translationally inactive, and/or (b) produces a non-functional gene product. In some embodiments, the exogenous pckA gene fragment may comprise up to the full length pckA gene, the sequence of which is interrupted by the insertion of another gene or genes, e.g. a selection marker such as an antibiotic resistance gene, a pigment, or an autofluorescent protein. In some embodiments, the interrupting gene may be flanked by site-specific recombination sites on both ends. These flanking site-specific recombination sites may or may not be contiguous with the interrupting gene. In some embodiments, the exogenous pckA gene fragment originates from the same species or strain of microorganism as the microorganism to be engineered according to the present invention. The sequence of the pckA gene fragment preferably has a sequence that is similar enough to the endogenous, wild-type, chromosomal pckA gene targeted so as to allow homologous recombination to occur Non-limiting examples of the antibiotic resistance gene used in for inactivation of the pckA gene include a chloramphenicol resistance gene, a kanamycin resistance gene, a gentamycin resistance gene, and an ampicillin resistance gene.

On the other hand, after a pckA gene-inactivated E. coli strain is selected, a site-specific recombinase may be expressed in the selected strain to remove the antibiotic resistance gene incorporated into the bacterial chromosome. That is, the antibiotic resistance gene is incorporated into the pckA gene on the bacterial chromosome along with site-specific recombinase binding sites, and removed by the activity of the site-specific recombinase expressed in the bacterial strain. Non-limiting examples of the site-specific recombinase include FLP, Cre and XerC/D. The removal of the antibiotic resistance gene allows the same antibiotic resistance gene to be used again as a selective marker when another gene of the identical bacterial strain is desired to be inactivated.

In the present invention, in order to inactivate the chromosomal pckA gene, a pckA gene fragment containing a chloramphenicol resistance gene, each end of which is linked to a loxP site, is used. The loxP sites, which are preferably in the same orientation, are recognized by a site-specific recombinase, Cre. The antibiotic resistance gene located between the two loxP sites may be excised from the bacterial chromosome by the activity of Cre recombinase expressed in the E. coli strain. In some embodiments of the invention, the loxP sites may be modified to prevent reintegration of the antibiotic resistance gene according to methods known in the art.

The Cre recombinase expression in the E. coli strain may be achieved by a method known in the art. In the present invention, a plasmid carrying a cre gene, pJW168, is introduced into the E. coli strain to express Cre enzyme therein.

In one embodiment of the present invention, a partial pckA gene was amplified by PCR using as a template genomic DNA isolated from a L-threonine-producing E. coli strain including an inactivated tdcBC operon. The amplified partial pckA gene was cloned into a pT7Blue vector (Novagen Co.), thus yielding a recombinant vector containing a partial pckA gene, pT7Blue/pckA. In addition, a DNA fragment containing a chloramphenicol resistance gene and loxP sites, loxpcat2, was obtained from a ploxpcat2 plasmid (Beatriz Palmeros et al., Gene, 247:255-264, 2000), and ligated to NruI-digested pT7Blue/pckA, thus generating a recombinant plasmid containing a pckA gene fragment that contains a chloramphenicol resistance gene and flanking loxP sites, pT7ΔpckA::loxpcat. Therefore, the present invention provides the recombinant plasmid as prepared above, pT7ΔpckA::loxpcat.

In another embodiment of the present invention, a suitable parental strain for tdcBC/pckA gene-inactivated E. coli strains of the invention is E. coli strain TRN212 having an inactivated tdcBC operon. In this parental strain, inactivation of the tdcBC operon is accomplished by homologous recombination using a kanamycin resistance gene having a loxP site at each of its both ends. To form microorganisms of the present invention, in some embodiments, a pckA gene fragment containing a chloramphenicol resistance gene, each end of which is linked to a loxP site, was introduced into E. coli strain TRN212 containing an inactivated tdcBC operon. Then, homologous recombination was allowed to occur between the pckA gene on the bacterial chromosome and the exogenous pckA gene fragment containing the chloramphenicol resistance gene and the loxP sites, thereby yielding a recombinant E. coli strain containing inactivated chromosomal tdcBC and pckA genes. A representative recombinant E. coli strain was designated as "FTR2717", and deposited under the Budapest Treaty at the Korean Culture Center of Microorganisms (KCCM), whose address is Hongje-dong, Seodaemun-gu, Seoul 120-749, on Mar. 20, 2003 and assigned Accession No. KCCM-10475.

The recombinant E. coli FTR2717 strain exhibits the following characteristics:

(1) it has resistance to threonine analogues, lysine analogues, isoleucine analogues, and methionine analogues compared to a wild type strain thereof;

(2) its chromosome contains an endogenousppc gene and an endogenous threonine operon containing thrA, thrB and thrC genes as well as one or more copies of an exogenous ppc gene and exogenous thrA, thrB and thrC genes;

(3) it includes an operon gene involved in L-threonine degradation, tdcBC, which is inactivated; and (4) it includes a pckA gene involved in inhibition of L-threonine synthesis, which is inactivated, so that it produces high levels of L-threonine under a high concentration of glucose in a medium.

In some embodiments, tdcBC/pckA gene-inactivated E. coli strains of the invention produce about 1% more, about 2% more, about 3% more, about 4% more, about 5% more, about 6% more, about 7% more, about 8% more, about 9% more, about 10% more, about 11% more, about 12% more, or about 13% more L-threonine than (a) a parent strain of Escherichia coli or (b) a corresponding wild-type strain of Escherichia coli cultured under substantially the same conditions. In some embodiments, tdcBC/pckA gene-inactivated E. coli strains of the invention produce about 6.5% more or about 13% more L-threonine than (a) a parent strain of Escherichia coli or (b) a corresponding wild-type strain of Escherichia coli cultured under substantially the same conditions.

A better understanding of the present invention may be obtained through the following examples which are set forth to illustrate, but are not to be construed as the limit of the present invention.

EXAMPLES

Example1

Cloning of pckA Gene

A recombinant vector carrying a pckA gene was prepared (see, FIG. 1). First, bacterial genomic DNA was isolated from a L-threonine-producing E. coli strain TRN212 (accession number: KCCM-10353), having an inactivated tdcBC operon, using a QIAGEN Genomic-tip system (QIAGEN Co.). Using the isolated genomic DNA as a template, PCR was carried out to amplify a region of the pckA gene of about 1.5-kb. The PCR included a forward primer having the sequence of SEQ ID NO:1 and a reverse primer having the sequence of SEQ ID NO:2. Amplification proceeded for 30 cycles wherein each cycle consisted of denaturation at 94° C. for 30 seconds, annealing at 55° C. for 30 seconds, and extension at 72° C. for 90 seconds.

The PCR products were size-fractionated on a 0.8% agarose gel, and a 1.5-kb band was excised out from the gel. From the excised band, a 1.5-kb DNA fragment was purified using a DNA Gel Purification Kit (QIAGEN Co.), and cloned into an EcoRV-digested pT7Blue vector (Novagen Co.) by blunt end ligation at 16° C. This yielded a recombinant vector containing a partial pckA gene, pT7Blue/pckA. Then, an E. coli NM522 strain was transformed with the pT7Blue/pckA, and streaked on a solid medium (LB: 1% NaCl, 1% Tryptone, 0.5% Yeast extract) containing ampicillin (100 mg/L), followed by incubation at 37° C. overnight. Colonies grown on the solid medium were used to inoculate liquid medium containing ampicillin, (3 mL each) followed by incubation at 37° C. overnight. Plasmid DNA was isolated from the cultured bacteria using a QIAGEN mini prep kit (QIAGEN Co.), and analyzed for its size. Also, orientation of the pckA gene was analyzed by restriction mapping with NruI and StuI. Thereafter, the plasmid DNA was digested with NruI, and size-fractionated on a 0.7% agarose gel. A slice of the gel at about 4.3-kb was excised and a 4.3-kb DNA fragment was purified from the gel slice.

Example 2

Figure 2:
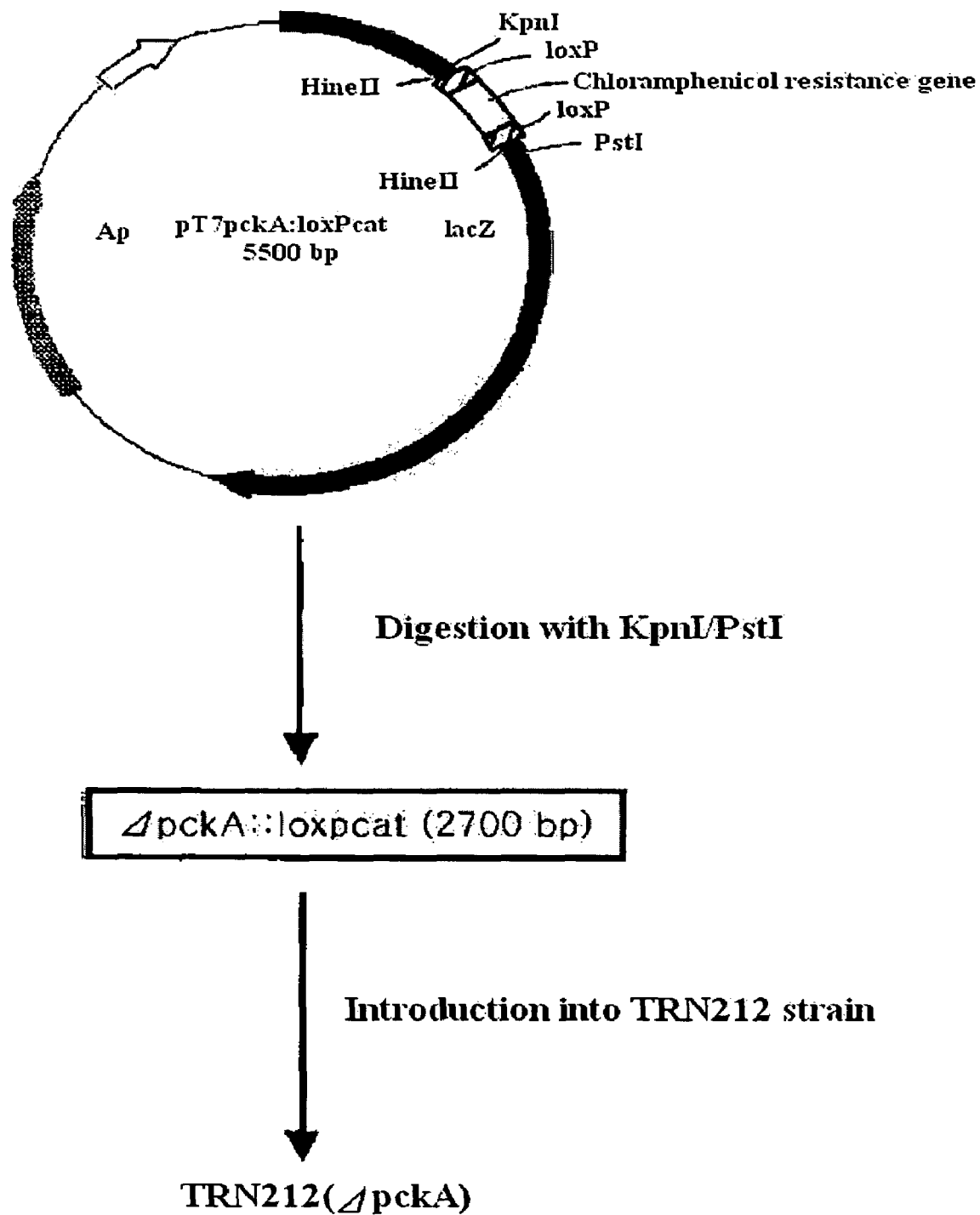
FIG. 2 is a schematic view showing a process of preparing a recombinant microorganism into which apckA gene fragment containing a chloramphenicol resistance gene (cat) and loxP sites, ΔpckA::loxpcat, is introduced.

Construction of Recombinant Vector Carrying an Inactivated pckA Gene and Preparation of pckA Gene-inactivated *E. coli* Strain 2-1) Construction of a Recombinant Vector Carrying an Inactivated pcka Gene A 1.2-kb DNA fragment, loxpcat, which contains a chloramphenicol resistance gene having a loxP site at each of its both ends was obtained by digesting with HincII a ploxpcat2 plasmid (plasmid carrying a chloramphenicol resistance gene having loxP sites at its both ends; Beatriz Palmeros et al., Gene, 247:255-264, 2000, Professor G. Gosset, University of Mexico). The 1.2-kb DNA fragment was ligated to the NruI-digested pT7Blue/pckA prepared in Example 1 by blunt end ligation, thus yielding an about 5.7-kb recombinant vector containing an inactivated pckA gene, pT7ΔpckA::loxpcat (see, FIG. 2).

2-2) Preparation of a pckA Gene-inactivated *E. coli* Strain

The pT7ΔpckA::loxpcat recombinant vector, prepared in Example 2-1), was introduced into an *E. coli* NM522 strain. The transformed NM522 strain was streaked on a solid medium (LB: 1% NaCl, 1% Tryptone, 0.5% Yeast extract) containing ampicillin and chloramphenicol, followed by incubation at 37° C. overnight. The colonies grown on the solid medium were inoculated in 3 mL of a liquid medium containing ampicillin and chloramphenicol, followed by incubation at 37° C. overnight. Plasmid DNA was isolated from the cultured bacteria using a QIAGEN mini prep kit, and analyzed for its size and orientation of the inserted pckA gene. Thereafter, the plasmid DNA was double-digested with PstI and KpnI, and size-fractionated on a 0.7% agarose gel. A slice of the gel at about 2.7-kb was excised and a 2.7-kb DNA fragment (ΔpckA::loxpcat) was purified from the gel slice.

The pckA gene fragment containing a chloramphenicol resistance gene having loxP sites at its both ends, ΔpckA::loxpcat, was introduced into a L-threonine-producing *E. coli* strain, TRN212 (accession number: KCCM-10353), by electroporation. Thereafter, the transformed TRN212 strain was streaked on a solid medium containing sufficient chloramphenicol to select only chloramphenicol-resistant cells, i.e. to select cells wherein a pckA gene on chromosome was replaced with the foreign pckA gene fragment (ΔpckA::loxpcat). The selected clones were evaluated for whether the chromosomal pckA gene is specifically knocked out, by Southern blot analysis according to the same method as in Example 3, below.

Clones identified as having a pckA gene specifically knocked out were transformed with a pJW168 plasmid (gift from Prof. Guillermo Gosset at the University of Mexico) that contains a cre gene encoding a site-specific recombinase recognizing loxP sites. The transformed cells were cultured in a culture medium containing 10 mM L-arabinose overnight. These conditions permit site-specific recombination to occur, resulting in the removal of the chloramphenicol resistance gene incorporated into the bacterial chromosome. Then, the culture fluid was diluted $10^7$-fold and spread on a solid LB medium supplemented with ampicillin (100 mg/L), followed by incubation at 30° C. overnight. Each of 100 colonies grown on the solid medium was inoculated in 3 mL of each of LB liquid media containing ampicillin or not, followed by incubation at 30° C. overnight. Colonies that were killed in the medium containing chloramphenicol but survived in the medium not containing chloramphenicol were determined. In this selection, only clones having a deletion of the chloramphenicol resistance gene were selected.

Example 3

Evaluation of Knock-out of pckA Gene on Chromosome by Southern Blotting

The parental TRN212 strain and one of the chloramphenicol-resistant clones selected in Example 2-2) were cultured overnight in 3 mL of a liquid medium containing chloramphenicol (15 mg/L). Then, genomic DNA was isolated from the culture cells using a QIAGEN genomic kit 20, and was digested with EcoRV overnight. The resulting DNA fragments were separated on a 0.7% agarose gel according to their size. After electrophoresis, the separated DNA fragments were transferred onto a nylon membrane (Biodyne B membrane, Young Sci.) overnight by capillary transfer (Molecular Cloning, Vol 1., pp6.31-6.38). The membrane was dried and then exposed to an UV light (120 mJ/cm$^2$, SpectroLinker™) to immobilize the DNA fragments on the membrane (Molecular Cloning, Vol 1., pp6.45). The resulting membrane was incubated in a prehybridization solution I (Roche #1093657) at 55° C. for 2 hours, and hybridized with a denatured DNA probe overnight in a hybridization oven (BAMBINO 230300) at 55° C.

The DNA probe was prepared as follows. First, a ploxpcat2 plasmid was isolated using a QIAGEN kit and digested with HincII to yield a DNA fragment (about 1.2 kb) containing a chloramphenicol resistance gene having a loxP site at each of its both ends. The 1.2-kb fragment was boiled in water for 5 minutes and quick-cooled on ice, thus yielding a single-stranded DNA. The single-stranded DNA was then labeled with DIG-UDP using a DIG Labeling and Detection Kit (Roche #1093657) by incubation at 37° C. overnight.

After hybridization, the membrane was washed with washing solutions I and II (Roche #1093657) to remove non-specifically attached DNA molecules. The washed membrane was masked using a prehybridization solution II (Roche #1093657) at room temperature for 30 minutes, and then reacted with an anti-DIG antibody specifically binding to DIG-UTP at room temperature for 30 minutes. The membrane was washed with a washing solution III (Roche #1093657) to remove non-specifically attached anti-DIG antibodies, and developed using a Labeling and Detection Kit (Roche #1093657) at room temperature until bands were emerged. The results are given in FIG. 3.

Figure 3:
FIG. 3 is a photograph showing a result of Southern blotting, in which a chloramphenicol resistance gene(cat) is identified to be inserted into a pckA gene on the chromosome of an L-threonine-producing E. coli strain (lane 1: recombinant strain selected in the presence of chloramphenicol according to the present invention; lane2: parent strain TRN212; and lane 3: size marker).

As shown in FIG. 3, in case of the parent strain TRN212, no band was detected (lane 2) because the TRN212 strain did not contain a chloramphenicol resistance gene. In contrast, the chloramphenicol-resistant clone selected according to the present invention showed an about 3.6-kb band (lane 1). These results indicate that the selected clones contain a chloramphenicol resistance gene on its chromosome.

Example 4

Comparison of the Selected Clones for Production Yields of L-threonine upon Culturing in Erlenmeyer Flasks Among the finally selected recombinant *E. coli* clones of Example 2-2) in which the introduced chloramphenicol resistance gene was removed, thirty clones were evaluated for L-threonine productivity. Each of them was cultured in an Erlenmeyer flask containing a culture medium prepared according to the composition listed in Table 1, below. Then, each culture fluid was evaluated for L-threonine yield. In brief, after each of the thirty clones were grown on a LB solid medium at 32° C., one loop of a single colony for each clone was inoculated in 25 mL of the culture medium and cultured at 32° C. for 48 hours at 250 rpm. After each of the culture fluids was centrifuged, the supernatant was 250-fold diluted with distilled water. L-threonine concentration in the diluted supernatant was measured by HPLC. The results are given in Table 2, below.

TABLE 1

| Nutrients | Amount per 1 L |
|---|---|
| Glucose | 70 g |
| Ammonium sulfate | 28 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| Calcium carbonate | 30 g |

TABLE 1-continued

| Nutrients | Amount per 1 L |
|---|---|
| L-methionine | 0.15 g |
| Yeast extract | 2 g |
| pH (7.0) | |

TABLE 2

| The number of clones | 2 | 5 | 14 | 9 |
|---|---|---|---|---|
| Production yield of L-threonine (g/L) | 20-23 | 23-24.5 | 24.5-26 | >26 |

The parent strain TRN212 showed a L-threonine production yield of 23 g/L. Among the thirty tested clones, twenty-eight were found to have better productivity of L-threonine than the TRN212 strain, as shown in Table 2. In particular, nine clones showed a L-threonine production yield higher than 26 g/L, which was about 13.04% higher than the yield of the TRN212 strain. Among the thirty clones, one clone with the highest yield of L-threonine (over 26 g/L) was selected and designated as "FTR2717 (accession number: KCCM-10475)".

DOCUMENTS CITED

All sequences, publications, patents, patent applications or other published documents cited anywhere in this specification are herein incorporated in their entirety by reference to the same extent as if each individual sequence, publication, patent, patent application or other published document was specifically and individually indicated to be incorporated by reference.

What is claimed is:

1. An isolated *Escherichia coli* strain FTR2717 (Accession No. KCCM-10475).

* * * * *